United States Patent [19]

Rothaul et al.

[11] Patent Number: 4,963,549

[45] Date of Patent: Oct. 16, 1990

[54] MEDICAMENT

[76] Inventors: Alan L. Rothaul; Lars M. Wood; Robert W. Gristwood, all of SmithKline Beckman Corporation, Corporate Patents N-160, P.O. Box 7929, Philadelphia, Pa. 19101

[21] Appl. No.: 250,043

[22] Filed: Sep. 27, 1988

[30] Foreign Application Priority Data

Sep. 28, 1987 [GB] United Kingdom ................. 8722776

[51] Int. Cl.$^5$ .............................................. A61K 31/50
[52] U.S. Cl. .................................... 514/247; 514/821
[58] Field of Search ................................ 514/247, 821

[56] References Cited

U.S. PATENT DOCUMENTS 4,654,342 3/1987 Slater .................................... 514/247

*Primary Examiner*—Frederick E. Waddell
*Attorney, Agent, or Firm*—James M. Kanagy; Stuart R. Suter; Edward T. Lentz

[57] ABSTRACT

The present invention relates to the use of 6-[4-($N^3$-methyl-$N^2$-cyanoguanidino)phenyl]-5-methyl-4,5-dihydro-3-(2H)-pyridazinone in a method of treating or preventing cardiac arrhythmias.

1 Claim, No Drawings

MEDICAMENT

The present invention relates to a method of treating or preventing cardiac arrhythmias by administering pharmaceutical compositions containing 6-[4-($N^3$-methyl-$N^2$-cyanoguanidino)phenyl]-5-methyl-4,5-dihydro-3(2H)pyridazinone.

This compound has previously been disclosed in U.S. Pat. No. 4,654,342 as a selective phosphodiesterase type III inhibitor with positive inotropic, vasodilator, bronchodilator and platelet aggregation inhibitory activities. The major utility disclosed in U.S. Pat. No. 4,654,342 for this compound is in the treatment of congestive heart failure. It has now been found that this compound possesses useful anti-arrhythmic properties not disclosed in U.S. Pat. No. 4,654,342.

According to the present invention there is provided a method of treating or preventing cardiac arrhythmias which comprises administering an effective amount of a pharmaceutical composition comprising 6-[4-($N^3$-methyl-$N^2$-cyanoguanidino)phenyl]-5-methyl-4,5-dihydro-3(2H)pyridazinone or a pharmaceutically acceptable salt thereof, and a pharmaceutically acceptable carrier.

In order to use 6-[4-($N^3$-methyl-$N^2$-cyanoguanidino)phenyl]-5-methyl-4,5-dihydro-3(2H)-pyridazinone or a pharmaceutically acceptable salt thereof for the treatment of humans and other mammals it is normally formulated in accordance with standard pharmaceutical practice as a pharmaceutical composition.

6-[4-($N^3$-Methyl-$N^2$-cyanoguanidino)phenyl]-5-methyl-4,5-dihydro-3(2H)-pyridazinone and pharmaceutically acceptable salts thereof may be administered in standard manner for the treatment of the indicated diseases, for example orally, parenterally, trans-dermally, rectally, via inhalation or via buccal administration. Preferably 6-[4-($N^3$-methyl-$N^2$-cyanoguanidino)phenyl]-5-methyl-4,5-dihydro-3(2H)-pyridazinone is administered orally.

6-[4-($N^3$-Methyl-$N^2$-cyanoguanidino)phenyl]-5-methyl-4,5-dihydro-3(2H)-pyridazinone and pharmaceutically acceptable salts thereof which are active when given orally or via buccal administration can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, lactose and sucrose. Where the composition is in the form of a capsule, any routine encapsulation is suitable, for example using the aforementioned carriers in a hard gelatin capsule shell. Where the composition is in the form of a soft gelatin shell capsule, any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

A typical suppository formulation comprises 6-[4-($N^3$-methyl-$N^2$-cyanoguanidino)phenyl]-5-methyl-4,5-dihydro-3(2H)-pyridazinone or a pharmaceutically acceptable salt thereof which is active when administered in this way, with a binding and/or lubricating agent, for example polymeric glycols, gelatins, cocoa-butter or other low melting vegetable waxes or fats.

Typical transdermal formulations comprise a conventional aqueous or non-aqueous vehicle, for example a cream, ointment, lotion or paste or are in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane.

Preferably the composition is in unit dosage form, for example a tablet, capsule or metered aerosol dose, so that the patient may administer to himself a single dose.

Each dosage unit for oral administration contains suitably from 0.01 mg/Kg to 3 mg/Kg, and preferably from 0.05 mg/Kg to 1.5 mg/Kg, and each dosage unit for parenteral administration contains suitably from 0.001 mg/Kg to 1 mg/Kg, of 6-[4-($N^3$-methyl-$N^2$-cyanoguanidino)phenyl]-5-methyl-4 5-dihydro-3(2H)-pyridazinone or a pharmaceutically acceptable salt thereof calculated as the free base.

The daily dosage regimen for oral administration is suitably about 0.01 mg/Kg to 12 mg/Kg, of 6-[4-($N^3$-methyl-$N^2$-cyanoguanidino)phenyl]-5-methyl-4,5-dihydro3(2H)-pyridazinone or a pharmaceutically acceptable salt thereof calculated as the free base. The daily dosage regimen for parenteral administration is suitably about 0.001 mg/Kg to 4 mg/Kg, for example about 0.01 mg/Kg to 1 mg/Kg, of 6-[4-($N^3$-methyl-$N^2$-cyanoguanidino)phenyl]-5-methyl-4, 5-dihydro-3(2H)-pyridazinone or a pharmaceutically acceptable salt thereof calculated as the free base. The active ingredient may be administered from 1 to 4 times a day.

The compositions of the present invention have anti-arrhythmic activity and are of use in the treatment and prevention of cardiac arrhythmias. Such conditions can be treated by administration orally, rectally, parenterally or by inhalation. For administration by inhalation dosages are controlled by a valve and are conveniently in the range 0.1–5.0 mg of 6-[4-($N^3$-methyl-$N^2$-cyanoguanidino)phenyl]-5-methyl-4,5-dihydro-3(2H)pyridazinone or a pharmaceutically acceptable salt thereof.

The compound of this invention may be co-administered with other pharmaceutically active compounds, for example in combination concurrently or sequentially. Conveniently the compound of this invention and the other active compound or compounds are formulated in a pharmaceutical composition. Examples of compounds which may be included in pharmaceutical compositions with 6-[4-($N^3$-methyl-$N^2$-cyanoguanidino)phenyl]-5-methyl-4,5-dihydro-3(2H)-pyridazinone are vasodilators for example hydralazine, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, cardioglycosides for example digoxin and digitoxin, calcium antagonists for example verapamil and nifedipine, diuretics such as thiazides and related compounds for example bendrofluazide, chlorothiazide, chlorothalidone, hydrochlorothiazide, and other diuretics for example frusemide and triamterene, and sedatives for example nitrazepam, flurazepam and diazepam.

6-[4-($N^3$-Methyl-$N^2$-cyanoguanidino)phenyl]-5-methyl-4,5-dihydro-3(2H)-pyridazinone and pharmaceutically acceptable salts thereof can be prepared by the methods disclosed in U.S. Pat. No. 4,654,342.

The following biological test method, data and Examples serve to illustrate this invention.

The anti-arrhythmic activity of 6-[4-($N^3$-methyl-$N^2$-cyanoguanidino)phenyl]-5-methyl-4,5-dihydro-3(2H)pyridazinone is demonstrated in the following test system.

Male New Zealand white rabbits were anaesthetised with Saffan 12 mg i.v. and α-chloralose 100 mg kg$^{-1}$. The active consitutents of Saffan, which is a trade mark of Glaxovet Limited, Uxbridge, UK, are alphaxalone and alphadolone acetate solubilised in saline by 20% w/v polyoxyethylated castor oil. The carotid artery and jugular vein were cannulated for phasic blood pressure measurement and drug administration. Limb lead II E.C.G. (electrocardiogram) was monitored. The chest was opened at the 4th intercostal space. Ligatures were placed under the circumflex artery close to its origin and the left anterior descending artery (LAD) at a point close to the margin of the atrial appendage. Animals in which this procedure reduced blood pressure below 60 mmHg, resulted in arrhythmia, or resulted in E.C.G. S-T segment changes consistent with ischaemia, were rejected. The animals were then allowed to stabilise for 15 minutes. In the drug treated group (selected randomly) racemic 6-[4-($N^3$-methyl-$N^2$-cyano-guanidino)phenyl]-5-methyl-4,5-dihydro-3(2H)-pyridazinone (compound A), 31.6 μg.kg$^{-1}$ i.v., resulted in a significant increase in heart rate (268±7 to 285±9 bpm, Student's t-test P<0.001) but had no effect on mean blood pressure (75±7 to 76±5 mmHg). After 15 minutes the circumflex artery was occluded resulting in a marked E.C.G. S-T segment changes indicative of ischaemia. Animals surviving 20 minutes (4 control, 7 drug) were subjected to LAD occlusion resulting in further E.C.G. changes. Rabbits surviving 20 minutes (3 control, 6 drug) then had the circumflex artery reperfused followed by LAD reperfusion 5 minutes later (1 death in control group, 0 death in drug treated group).

The results of these experiments are shown in the table below. As can be seen compound A had no significant effect on the mean number of ventricular ectopic beats (VEB) or on the duration of ventricular tachycardia (VT). However, compound A significantly reduced the incidence of ventricular fibrillation and consequently markedly reduced mortality.

Figures represent mean values±SEM (standard error of the mean), those in brackets show number of animals exhibiting this arrhythmia, individual values are shown where this is less than 3, Student's t-test P<0.05.

| Group | N | VEB | VT | VENTRICULAR FIBRILLATION % | MORTALITY % |
|---|---|---|---|---|---|
| Control | 10 | 158 ± 55(10) | 29,8(2) | 80 | 80 |
| Compound A | 9 | 137 ± 59(9) | 159 ± 144(3) | 44* | 33* |

*Fischers Exact test (two sided) P value <0.05

Thus, these data indicate that compound A is cardioprotective against ischaemia and reperfusion induced fibrillation and reduces mortality in this model. Compound A is therefore useful as an anti-arrhythmic agent and has utility in the treatment of congestive heart failure associated with myocardial ischaemia.

Example 1

A pharmaceutical composition for parenteral administration was prepared by dissolving 6-[4-($N^3$-methyl-$N^2$-cyanoguanidino)phenyl]-5-methyl-4,5-dihydro-3(2H)-pyridazinone (0.02 g) in polyethylene glycol 300 (25 ml) with heating. This solution was then diluted with water for injections E.p. (to 100 ml). The solution was then sterilised by filtration through a 0.22 micron membrane filter and sealed in sterile containers.

Compositions containing 6-[4-($N^3$-methyl-$N^2$-cyanoguanidino)phenyl]-5-methyl-4,5-dihydro-3(2H)-pyridazinone (0.04 g) in polyethylene glycol 300 were prepared in analogous manner.

Example 2

A pharmaceutical composition for oral administration was prepared by combining the following:

| | % w/w | | |
|---|---|---|---|
| 6-[4-($N^3$-Methyl-$N^2$-cyano-guanidino)phenyl]-4,5-dihydro-5-methyl-3(2H)-pyridazinone, | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulation was then filled into individual soft gelatin capsules.

What is claimed is:

1. A method of treating ventricular fibrillation in a mammal suffering from same, which method comprises administering an effective amount of a pharmaceutical composition comprising 6-[4-($N^3$-methyl-$N^2$-cyanoguanidino)phenyl]-5- methyl-4,5-dihdro-3(2H)-pyridazinone or a pharmaceutically acceptable salt thereof, and a pharmaceutically acceptable carrier.

* * * * *